US00PP14530P29

(12) United States Plant Patent
Strope

(10) Patent No.: US PP14,530 P2
(45) Date of Patent: Feb. 10, 2004

(54) PETUNIA PLANT NAMED 'BALSUNDEUM'

(50) Latin Name: *Petunia×hybrida*
Varietal Denomination: Balsundeum

(75) Inventor: Kerry M. Strope, Jefferson City, MO (US)

(73) Assignee: Ball Horticultural Company, West Chicago, IL (US)

( * ) Notice: Subject to any disclaimer, the term of this patent is extended or adjusted under 35 U.S.C. 154(b) by 0 days.

(21) Appl. No.: 10/361,886

(22) Filed: Feb. 10, 2003

(51) Int. Cl.[7] ..... A01H 5/00
(52) U.S. Cl. ..... Plt./356
(58) Field of Search ..... Plt./356

*Primary Examiner*—Bruce R. Campell
*Assistant Examiner*—Susan B. McCormick
(74) *Attorney, Agent, or Firm*—C. A. Whealy

(57) ABSTRACT

A new and distinct cultivar of Petunia plant named 'Balsundeum', characterized by its upright, outwardly spreading and mounded plant habit; freely basal branching habit; and single flowers that are purple in color.

1 Drawing Sheet

Botanical classification/cultivar designation: *Petunia×hybrida* cultivar Balsundeum.

BACKGROUND OF THE INVENTION

The present Invention relates to a new and distinct cultivar of Petunia plant, botanically known as *Petunia×hybrida*, and hereinafter referred to by the cultivar name Balsundeum.

The new Petunia is a product of a planned breeding program conducted by the Inventor in Arroyo Grande, Calif. The objective of the breeding program is to create new freely branching Petunias with large flowers and attractive flower coloration.

The new Petunia originated from a cross pollination made by the Inventor in 2000 of a proprietary *Petunia×hybrida* selection identified as code number 464C, not patented, as the female, or seed parent, with a proprietary *Petunia×hybrida* selection identified as code number 462C, not patented, as the male, or pollen parent. The new Petunia was selected as a single plant from the resulting progeny by the Inventor in Arroyo Grande, Calif.

Asexual reproduction of the new cultivar by terminal vegetative cuttings taken in Arroyo Grande, Calif. since December, 2000 has shown that the unique features of this new Petunia are stable and reproduced true to type in successive generations.

SUMMARY OF THE INVENTION

Plants of the cultivar Balsundeum have not been observed under all possible environmental conditions. The phenotype may vary somewhat with variations in environment such as temperature and light intensity without, however, any variance in genotype.

The following traits have been repeatedly observed and are determined to be the unique characteristics of 'Balsundeum'. These characteristics in combination distinguish 'Balsundeum' as a new and distinct cultivar:

1. Upright, outwardly spreading and mounded plant habit.
2. Freely basal branching habit.
3. Single flowers that are purple in color.

Plants of the new Petunia differ from plants of the parent selections in plant habit, flower form and flower coloration.

Plants of the new Petunia can be compared to plants of the cultivar Dancascharl, not patented. In side-by-side comparisons conducted in West Chicago, Ill., plants of the new Petunia differed from plants of the cultivar Dancascharl in the following characteristics:

1. Plants of the new Petunia were taller than but not as outwardly spreading as plants of the cultivar Dancascharl.
2. Plants of the new Petunia had longer leaf petioles than plants of the cultivar Dancascharl.
3. Plants of the new Petunia were more floriferous than plants of the cultivar Dancascharl.

BRIEF DESCRIPTION OF THE PHOTOGRAPHS

The accompanying colored photographs illustrate the overall appearance of the new cultivar, showing the colors as true as it is reasonably possible to obtain in colored reproductions of this type. Colors in the photographs may differ slightly from the color values cited in the detailed botanical description which accurately describe the colors of the new Petunia.

The photograph at the top of the sheet comprises a side perspective view of a typical flowering plant of 'Balsundeum'.

The photograph at the bottom of the sheet is a close-up view of a typical flower of 'Balsundeum'.

DETAILED BOTANICAL DESCRIPTION

The cultivar Balsundeum has not been observed under all possible environmental conditions. The phenotype may vary somewhat with variations in environment such as temperature and light intensity without, however, any variance in genotype.

The aforementioned photographs, following observations and measurements describe plants grown in West Chicago, Ill., under commercial practice in a polycarbonate-covered greenhouse. Plants were about 14 weeks from rooted cuttings and were grown in 10-cm containers. During the production of the plants, day temperatures ranged from 14 to 24° C., night temperatures ranged from 11 to 17° C. and light levels ranged from 5,000 to 8,000 foot-candles.

In the following description, color references are made to The Royal Horticultural Society Colour Chart, 2001 Edition, except where general terms of ordinary dictionary significance are used.

Botanical classification: *Petunia×hybrida* cultivar Balsundeum.

Parentage:

*Female parent.*—Proprietary *Petunia×hybrida* selection identified as code number 464C, not patented.

*Male parent.*—Proprietary *Petunia×hybrida* selection identified as code number 462C, not patented.

Propagation:

*Type cutting.*—Terminal vegetative cuttings.

*Time to initiate roots.*—About 7 days at 18° C.

*Time to develop roots.*—About 21 days at 18° C.

*Root description.*—Fibrous, whitish in color.

*Rooting habit.*—Freely branching.

Plant description:

*Form.*—Annual flowering plant; indeterminate; upright, outwardly spreading and mounded plant habit. Moderately vigorous.

*Plant height.*—About 28.8 cm.

*Plant diameter.*—About 60 cm.

*Branching habit.*—Freely basal branching with about eight lateral branches per plant.

*Lateral branches.*—Length: About 31.2 cm. Diameter: About 3 mm. Internode length: About 9 mm. Texture: Densely pubescent. Color: 144A.

*Foliage description.*—Arrangement: Before flowering, alternate; after flowering, opposite; simple. Quantity per lateral branch: About 19. Length: About 3.2 cm. Width: About 2 cm. Shape: Ovate. Apex: Acute. Base: Attenuate. Margin: Entire. Texture, upper and lower surfaces: Densely pubescent; velvety. Venation pattern: Pinnate. Color: Developing foliage, upper surface: 137B. Developing foliage, lower surface: 137C. Fully expanded foliage, upper surface: 137A. Fully expanded foliage, lower surface: 137C. Venation, upper surface: 144B. Venation, lower surface: 144C. Petiole length: About 1.2 cm. Petiole diameter: About 2 mm. Petiole color, upper and lower surfaces: 144C.

Flower description:

*Flower type and habit.*—Single salverform flowers; flowers face mostly upward or outward; axillary; about six flowers per lateral branch.

*Natural flowering season.*—Long day responsive; spring until frost in the autumn; flowering continuous. Plants start flowering about ten weeks after planting.

*Flower longevity on the plant.*—About five days; flowers persistent.

*Fragrance.*—None detected.

*Flower size.*—Diameter: About 5.4 cm. Tube length: About 2.3 cm. Throat diameter, distal end: About 1.1 cm. Tube diameter, proximal end: About 3 mm.

*Flower buds.*—Length: About 3.9 cm. Diameter: About 9 mm. Shape: Ovoid, tubular. Color: Closest to 83A.

*Corolla.*—Quantity/arrangement: Five fused petals; funnelform. Petal length from throat: About 2.1 cm. Petal width: About 2.6 cm. Petal shape: Roughly spatulate. Petal apex: Rounded. Petal margin: Entire; undulate. Petal texture, upper and lower surfaces: Smooth, glabrous; velvety. Petal color: When opening, upper surface: Much darker than N81A. When opening, lower surface: 77A. Fully opened, upper surface: Darker than N81A; color becoming close to N92C with development. Fully opened, lower surface: 77A. Flower throat (inside): 79A. Flower tube (outside): 83A. Venation, upper petal surface: 79A. Venation, lower petal surface: Midvein, 79A; lateral veins, 79B. Venation, throat: 79A. Venation, tube: 79B.

*Sepal.*—Arrangement/appearance: Single whorl of five sepals fused at base, star-shaped. Length: About 1 cm. Width: About 2.5 mm. Shape: Linear. Apex: Rounded to broadly acute. Margin: Entire. Texture, upper and lower surfaces: Densely pubescent. Color: Upper surface: 137A. Lower surface: 137C; towards the base, 183A.

*Peduncles.*—Length: About 1.2 cm. Width: About 1 mm. Angle: Acute, about 45° from vertical. Strength: Moderately strong. Texture: Pubescent. Color: 144A.

*Reproductive organs.*—Stamens: Quantity per flower: About five. Anther shape: Ovoid. Anther length: About 2 mm. Anther color: 79D. Pollen amount: Abundant. Pollen color: 91A. Pistils: Quantity per flower: One. Pistil length: About 2 cm. Style length: About 1.5 cm. Style color: 145C; towards stigma, N88B. Stigma shape: Funnel. Stigma length: About 4 mm. Stigma color: N88A. Ovary color: 145A.

*Seed/fruit.*—Seed nor fruit production has not been observed.

Disease/pest resistance: Plants of the new Petunia have not been noted to be resistant to pathogens or pests common to Petunia.

It is claimed:

1. A new and distinct cultivar of Petunia plant named 'Balsundeum', as illustrated and described.

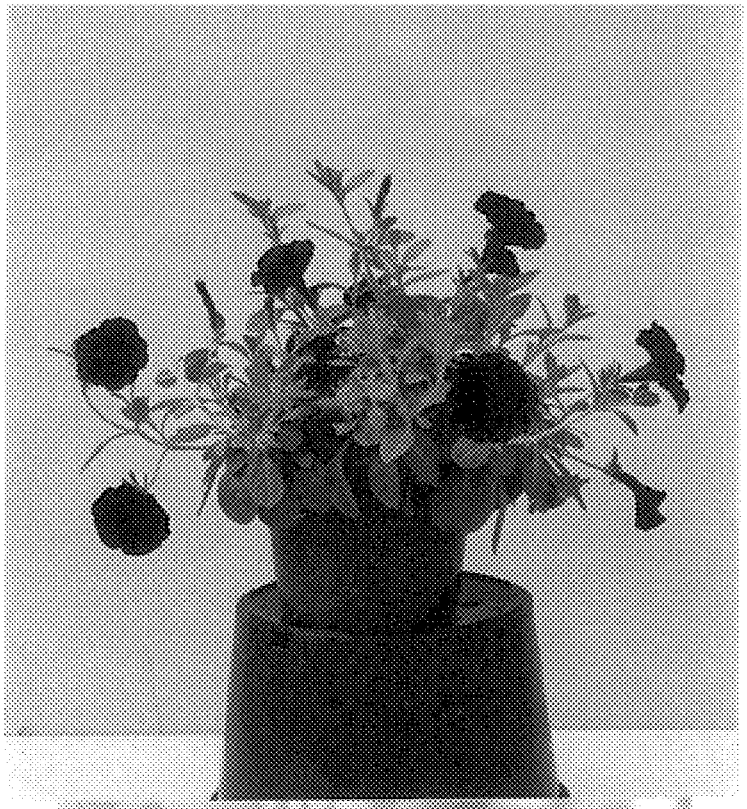
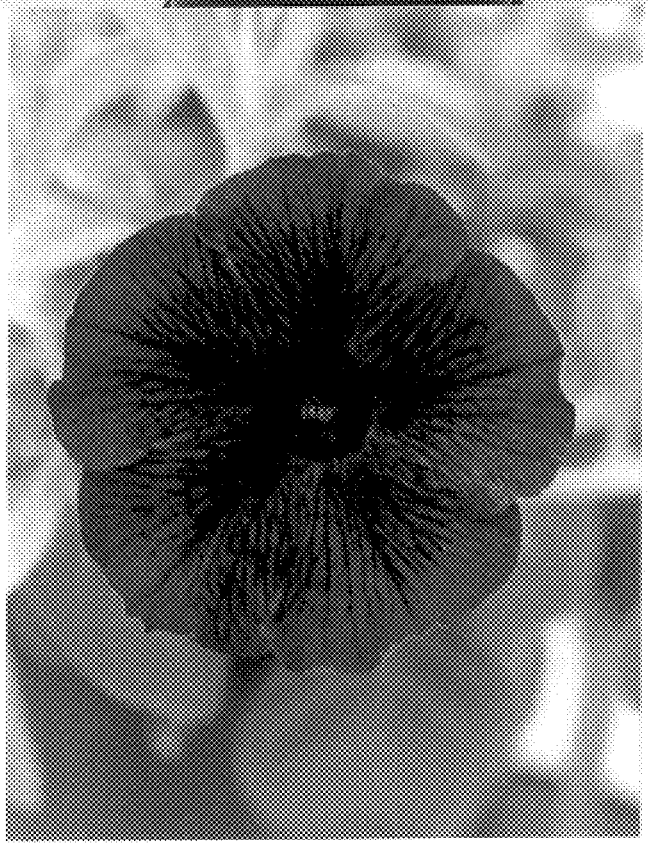

* * * * *